United States Patent [19]

Fink

[11] Patent Number: 5,532,157
[45] Date of Patent: Jul. 2, 1996

[54] HOST CELL LINE LVIP2.0ZC, USEFUL IN ASSAYS TO IDENTIFY LIGANDS AND ANT AGONISTS OF G PROTEIN-COUPLED RECEPTORS

[75] Inventor: J. Stephen Fink, Wellesley, Mass.

[73] Assignee: The United States of America as represented by the Secretary, Department of Health and Human Resources, Washington, D.C.

[21] Appl. No.: 176,310

[22] Filed: Jan. 3, 1994

Related U.S. Application Data

[63] Continuation of Ser. No. 768,053, Oct. 1, 1991, abandoned.
[51] Int. Cl.$^6$ ....................................................... C12N 5/10
[52] U.S. Cl. ........................ 435/240.2; 435/320.1; 435/7.21
[58] Field of Search .............................. 435/6, 7.1, 7.23, 435/240.2, 240.27, 69.1, 240.1, 7.21

[56] References Cited

U.S. PATENT DOCUMENTS 5,126,251  6/1992  Moss et al. ............................ 435/69.1

OTHER PUBLICATIONS

Konig et al. (1991) Mol Cell Neurosci vol. 2 (4). pp. 331–337.

*Primary Examiner*—Garnette D. Draper
*Assistant Examiner*—David L. Fitzgerald
*Attorney, Agent, or Firm*—Morgan & Finnegan

[57] ABSTRACT

The present invention relates, in general, to a method of identifying ligands and antagonists of ligands. In particular, the present invention relates to a method of identifying ligands and antagonists of ligands which bind to cloned $G_s$- or $G_i$-coupled receptors. The present invention also relates to a cell that comprises a recombinant cyclic AMP sensitive reporter construct.

1 Claim, 8 Drawing Sheets

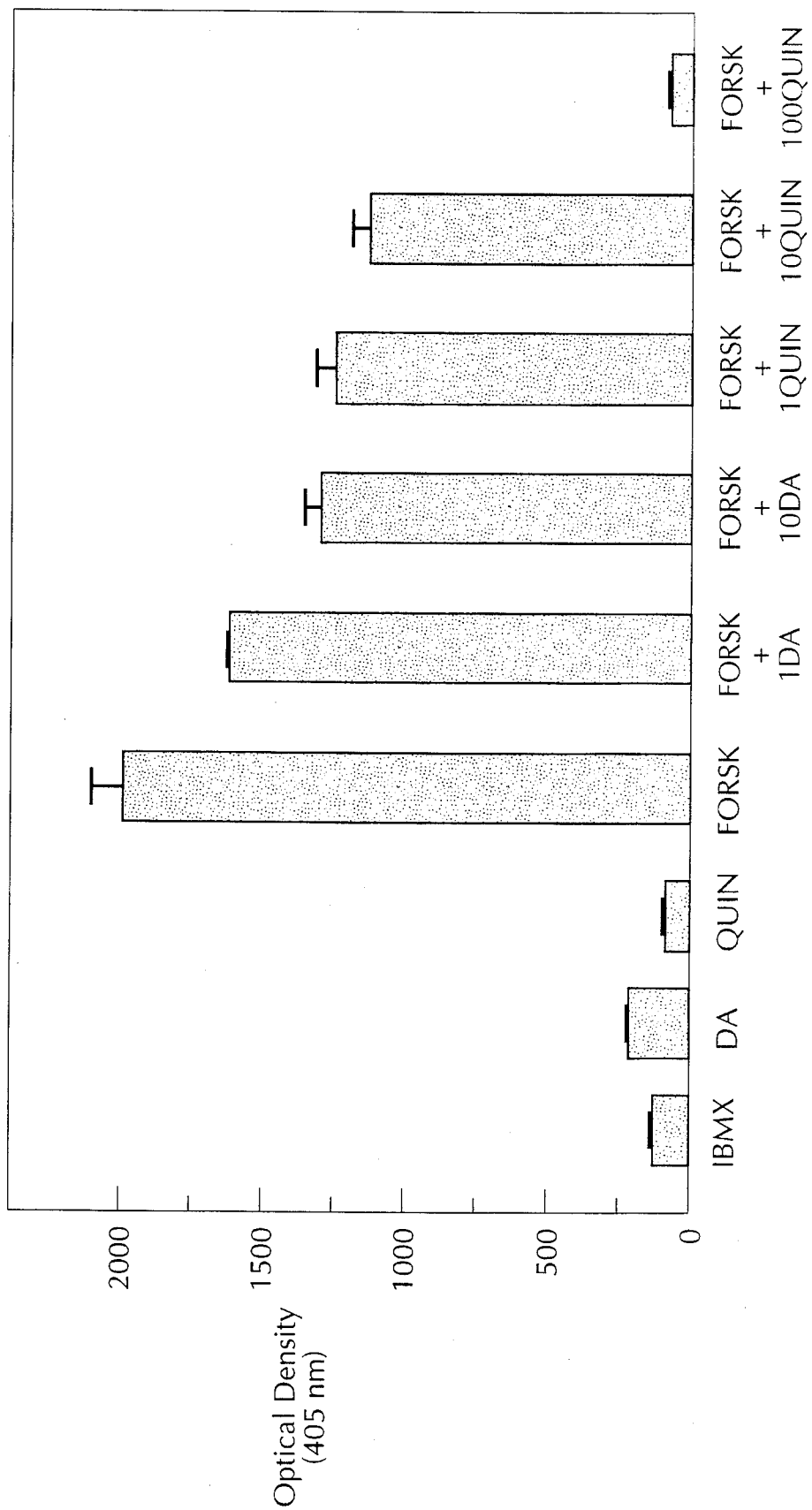

5,532,157

HOST CELL LINE LVIP2.0ZC, USEFUL IN ASSAYS TO IDENTIFY LIGANDS AND ANT AGONISTS OF G PROTEIN-COUPLED RECEPTORS

This is a continuation of application Ser. No. 07/768,053, filed on Oct. 1, 1991, now abandoned.

BACKGROUND OF THE INVENTION

1. Field of the Invention

The present invention relates, in general, to a method of identifying ligands and antagonists of ligands. In particular, the present invention relates to a method of identifying ligands and antagonists of ligands which bind to cloned $G_s$- or $G_i$-coupled receptors. The present invention also relates to a cell comprising a recombinant cyclic AMP sensitive reporter construct.

2. Background Information

In the last several years, numerous cDNAs or genes for hormones and neurotransmitters that couple to G-proteins have been cloned. With only two exceptions—the receptors for insulin-like growth factor II and glutamic acid—these G-coupled receptors are rather similar, and they are thought to comprise a large "superfamily" of proteins. By analogy to bacterial rhodopsin, the members of this superfamily are thought to contain seven membrane-spanning domains and have a number of highly conserved amino acids. As a consequence, oligonucleotide probes directed at shared domains of cloned receptors have been used at low stringency to screen cDNA libraries for novel receptor candidates. More recently, primers directed at conserved domains of these receptors have been used in the polymerase chain reaction to clone additional candidates. The cDNAs obtained as described above, which encode "orphan receptors" for which the endogenous ligand is not known, must be expressed and the ligands which the receptors bind must be identified. This is not as straightforward as it seems at first glance. Screening with radiolabelled ligands is expensive. It requires many (unstable) ligands and large amounts of transfected cells. Functional screens, on the other hand, are hampered by the fact that one cannot guess from the structure of a receptor which second messenger system it activates. Some G-protein coupled receptors activate phospholipase C or phospholipase $A_2$ and increase inositol phosphates and arachidonic acid, respectively. Others activate ($G_s$-coupled) or inhibit the activation ($G_i$-coupled) of adenylate cyclase, increasing or decreasing the level of cyclic AMP in cells. The present invention provides simple and rapid methods for discovering the agonists which act on orphan $G_s$- or $G_i$-coupled receptors.

The assay that has been developed employs a novel mouse L cell line, LVIP2.OZc. These L cells contain a stably integrated fusion gene pLVIP2.OZ plasmid (Riabowol, K.T. et al., (1988) Nature 336:83–86), consisting of the *Escherichia coli* lac Z gene under the transcriptional control of 2 kb fragment derived from the vasoactive intestinal polypeptide (VIP) gene. This DNA segment includes the VIP promoter and a cyclic AMP responsive enhancer element (CRE). Forskolin increases cellular cyclic AMP levels and thus can be used to induce the β-galactosidase enzyme in the LVIP2.OZc. reporter cells. After the cells are lysed, the enzyme activity can be detected by addition of a chromogenic substrate, o-nitrophenyl β-D-galactopyranoside (ONPG). The product of the reaction, o-nitrophenol, is yellow in color and can be seen with the naked eye or measured spectrophotometrically at a wavelength of 405 nm. The assay can be performed in 96 well tissue culture plates and a commercially available plate reader can be used to measure the levels of o-nitrophenol and record the results.

Transfection of cells with a putative $G_s$-coupled receptor allows one to induce the enzyme by adding the appropriate ligand. For example, cells transfected with a $β_2$-adrenergic receptor cDNA increase their β-galactosidase levels in response to isoproterenol. $G_i$-coupled receptors, on the other hand, inhibit the activation of adenylate cyclase. In the presence of the appropriate ligands the dopamine $D_{2L}$, muscarinic cholinergic $m_2$, or cannabinoid transfected receptors significantly reduce the forskolin-stimulated increase in β-galactosidase normally seen in LVIP2.OZc cells. Thus, LVIP2.OZc cells provide a rapid, convenient and semi-automated system in which a large number of putative ligands may be screened for binding to an "orphan receptor" transiently expressed in these cells.

SUMMARY OF THE INVENTION

It is a general object of this invention to provide a method of identifying ligands and antagonists of ligands.

It is a specific object of this invention to provide a method of identifying ligands which bind to G-protein coupled receptors.

It is another object of this invention to provide a method of identifying an antagonist of a ligand wherein the ligand binds to a G-protein coupled receptor.

It is a further object of this invention to provide a cell that comprises a recombinant cyclic AMP sensitive reporter construct.

Further objects and advantages of the present invention will be clear from the description that follows.

BRIEF DESCRIPTION OF THE DRAWINGS

from a representative experiment.

FIG. 6C) Inhibition for forskolin-mediated induction of β-galactosidase in human muscarinic acetylcholine ($hm_2$) receptor DNA transfected LVIP2.OZc cells by carbachol. Cells were exposed for 6 hours to medium containing 0.5 mM IBMX and 0.5 μM forskolin±mM carbachol. Data are mean±S.D. from one representative experiment.

DETAILED DESCRIPTION OF THE INVENTION

Figure 1:
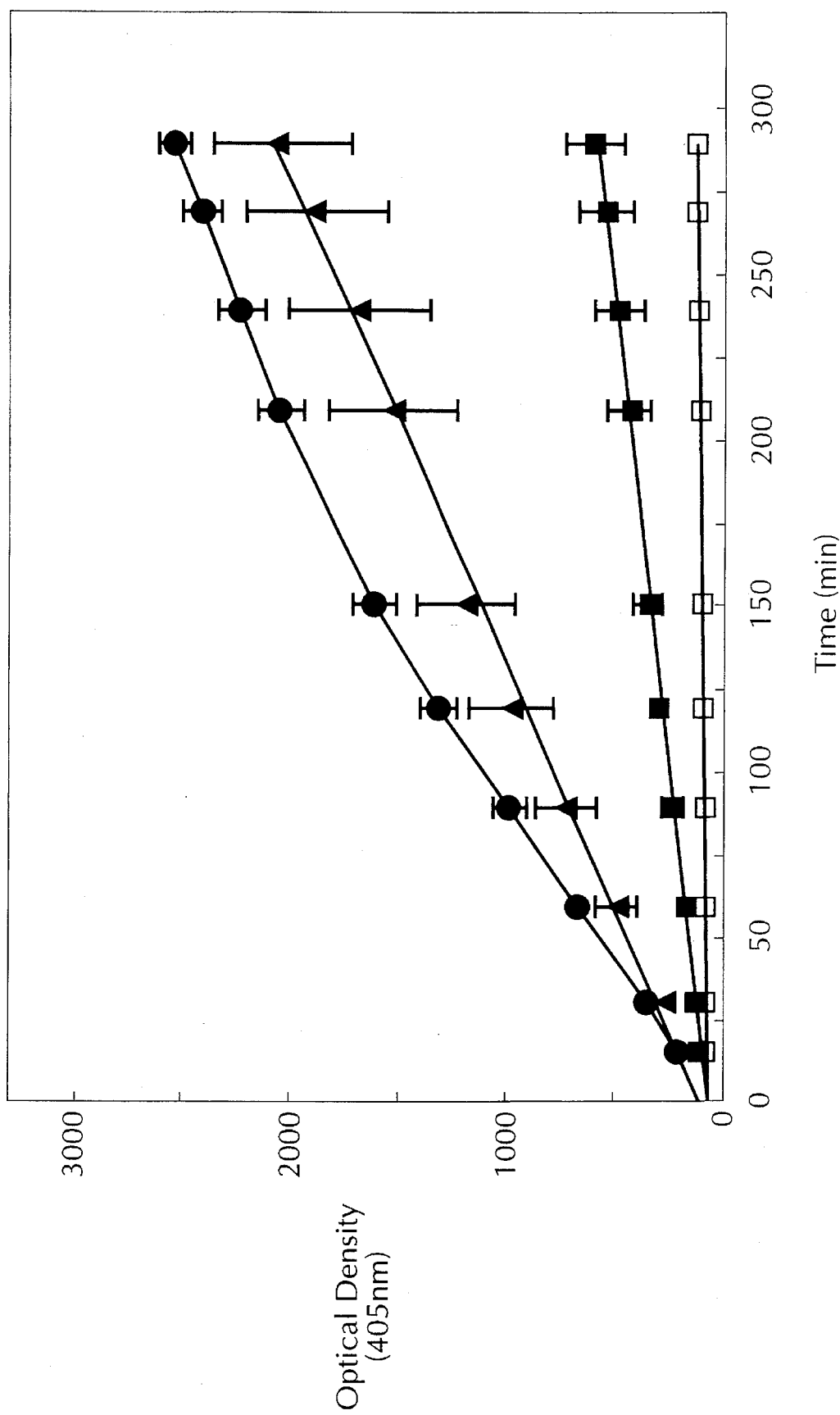
FIG. 1. Detection of β-galactosidase of color development of o-nitrophenol. LVIP2.OZc cells were exposed for 8 hours to control medium (containing 0.5 mM IBMX) (□), or control medium containing 0.5 μM forskolin (•), or control medium containing 1 μM (■) or 10 NECA (▲). After cell lysis and addition of the substrate ONPG, enzyme activity was measured as optical density at 405 nm at various time intervals. Data are mean±S.D. taken from one experiment that is representative of several.

The present invention relates to a fast, simple method to identify (1) ligands which bind to a G-protein coupled receptor and (2) antagonists of these ligands.

In one embodiment, the method comprises: i) expressing a $G_s$-coupled receptor gene in a cell wherein the cell contains a cyclic AMP sensitive reporter construct; ii) adding a ligand to the cell; and iii) assaying for the amount of cyclic AMP.

In general, the construct comprises a cyclic AMP responsive regulatory element operably linked to a reporter gene. In a preferred embodiment, the cyclic AMP sensitive reporter construct comprises a cyclic AMP responsive enhancer element operably linked to a promoter and a reporter gene. Suitable cyclic AMP responsible enhancer (CRE) elements are well known in the art. They include but are not limited to the CRE located on the 2 kb DNA fragment from the vasoactive intestinal polypeptide (VIP) gene. Suitable promoters are also well known in the art. They include but are not limited to the VIP promoter described herein. Further, suitable reporter genes are also well known in the art. They include but are not limited to: the Lac Z gene and the luciferase gene. Specifically, the reporter construct used may be pLVIP2.OZ.

The G-coupled receptor gene expressed in the cell may be stably incorporated into the genome of the cell, may be transiently transfected into the cell, or may be endogenous to the cell. Examples of G-coupled receptors include: the human $β_2$-adrenergic receptor; the human $m_2$ muscarinic acetylcholine receptor; the rat cannabinoid receptor; the dopamine $D_{2L}$ receptor; VIP; secretin; vasopressin; oxytocin; serotonin; α-adrenergic; metabolic glutamate; and IL-8 receptors.

Suitable host cells, if appropriate vectors are used, include both lower eucaryotes (for example, yeast) and higher eucaryotes (for example, mammalian cells—specifically, mouse cells). Preferably, the assay uses a mouse L cell line (for example—LVIP2.OZc, deposited on Sep. 18, 1991 with the American Type Culture Collection (ATCC), 12301 Parklawn Drive, Md., 20852 U.S.A. ATCC accession no. CRL 10871) which contains a cyclic AMP responsive reporter construct (for example—pLVIP2.OZ).

The methods of assaying for the expression of the reporter genes are well known in the art. In a preferred embodiment, the assaying step comprises adding a chromogenic substrate and assaying for a change in that substrate. One preferred chromogenic compound is o-nitrophenyl β-D-galactopyranoside.

In a further embodiment, the present invention relates to a method of identifying an antagonist of a ligand wherein the ligand binds to a G-protein coupled receptor. The method comprises: i) expressing a $G_s$-coupled receptor gene or cDNA in a cell wherein the cell contains a cyclic AMP sensitive reporter construct; ii) adding a ligand and antagonist to the cell; and iii) assaying for the amount of cyclic AMP. The cyclic AMP reporters, reporter genes, constructs, and cells described-above can be used to identify antagonists.

In a further embodiment, the present invention relates to a method of identifying a ligand that binds to a receptor which inhibits stimulation of adenylyl cyclase. The method comprises: i) expressing a $G_i$-coupled receptor gene of cDNA in a cell wherein the cell contains a cyclic AMP sensitive reporter construct; ii) adding forskolin and candidate ligands; and iii) assaying for the amount of cyclic AMP.

In a further embodiment, the present invention relates to a method of identifying an antagonist of a ligand that binds to a receptor which inhibits stimulation of adenylyl cyclase. The method comprises: i) expressing a $G_i$-coupled receptor or cDNA in a cell wherein the cell contains forskolin and a specific ligand and candidate antagonists; and iii) assaying for the amount of cyclic AMP, looking for the inhibition of agonist induced reduction of forskolin activity.

The method described herein can be used to screen large numbers of ligands: for example, as many as 22 ligands can be analyzed in quadruplicate in a single 96 well plate. The stimulation or inhibition of stimulation is easy to recognize, and positive results can quickly be confirmed.

The present invention is described in further detail in the following non-limiting Examples.

EXAMPLES

The following protocols and experimental details are referenced in the Examples that follow:
Materials.

Unless otherwise indicated, chemicals were obtained from SIGMA, culture media from Whittaker Bioproducts, ASIF (Aldosterone Secretion Inhibitory Factor) [Bovine] was purchased from PENINSULA LABORATORIES, ONPG (o-NITROPHENYL-β-D-galactopyranoside) was obtained from RESEARCH ORGANICS, (−)-Propanolol hydrochloride, Dopamine hydrochloride, (−)-Quinpirole hydrochloride were obtained from RBI, CP55940 was generously provided by PFIZER, INC.

Stable cell line and cell culture.

Mouse Ltk-cells ($3\times10^6$ per 10 cm dish) were transfected using the calcium phosphate co-precipitation method with the pLVIP2.OZ plasmid (20 μg) containing 2 kb of 5'-flanking sequences from the human VIP gene fused to the *E. coli* lac Z gene (Riabowol et al. (1988) Nature 336:83–86). Co-transfection with 4 μg phyg (Sugden et al. (1985) Mol. Cell. Biol. 5:410), a plasmid encoding hygromycin B phosphotransferase, and selection in hygromycin provided a dominant selectable marker. Hygromycin-resistant Ltk⁻ clones were screened for induction of β-galactosidase after addition of forskolin (10 μM) and IBMX (0.5 μM). One clone, LVIP2.OZc, was chosen for use in these experiments. LVIP2.OZc cells, stably transfected with the pLVIP2.OZ plasmid were maintained in Dulbecco modified Eagle medium (DMEM), supplemented with 2.5% fetal calf serum, 7.5% newborn calf serum, 25 mg/ml hygromycin, penicillin and streptomycin in a 7% $CO_2$ 37° Forma incubator. Cells were trypsinized twice weekly with 1 ml 0.5% Trypsin and 0.53 mM EDTA.4Na/10 cm dish and split at a ratio of 1:10 and grown in 10 ml medium over several months. The phenotype of the cells seems stable.

Plasmid DNA.

Plasmid DNA was prepared by the lysozyme-Triton procedure (Katz, L. et al., (1973) J. Bacteriol. 114:577–591) as modified for the transfection protocol of Chen and Okayama ((1987) Mol. Cell. Biol. 7:2745–2752). The following receptor cDNAs were introduced into the pcD plasmid (Okayama, H. et al., (1983) Mol. Cell. Biol. 3:280–289): the human $\beta_2$-adrenergic receptor (Kobilka, B.K. et al., (1987) PNAS 84:46–50), the human $m_2$ muscarinic acetylcholine receptor (Bonner, T.I. et al., (1987) Science 237:527–531), the rat cannabinoid receptor (Matsuda, L.A. et al., (1990) Nature 346:561–564). The dopamine $D_{2L}$ receptor (Monsma, F.J. et al., (1989) Nature 342:926–929) was subcloned into the pRc/RSV vector (INVITROGEN, eukaryotic vector).

Transfection of cells.

Cells were transfected by the calcium phosphate transfection protocol of Chen and Okayama. For each plasmid DNA preparation, the amount of DNA required for formation of an optimum calcium phosphate-DNA precipitate varies; thus, a dose response study is desirable. To set up conditions to assay $G_s$-coupled receptors, cells were transfected with various amounts (5 to 30 μg) of pcD plasmid DNA containing the human $\beta_2$-adrenergic receptor cDNA/ 10-cm plate. If smaller or larger dishes were used, the amount of DNA was adjusted proportionally. The precipitate formed with 5 μg of DNA usually was very coarse; with 25 to 30 μg of DNA the precipitate was usually very fine when observed with a microscope at low magnification (40 x). Eight to 20 μg gave a punctuate precipitate which seems to be taken up by the cells efficiently. Cells were trypsinized 48 hours after transfection, pelleted, resuspended in fresh medium, seeded into 96 well microtiter plates (flat bottom) at $5-10\times10^4$ cells/well in 100 μl medium, and incubated for an additional 24 hours. Then 100 μl of medium containing isoproterenol (2 μM), ascorbic acid (200 μM) and isobutyl methyl xanthine (1 mM) (IBMX, a phosphodiesterase inhibitor) was added to each well. Adding medium rather than replacing the medium in each well gave more reproducible results. One hundred microliters of medium containing IBMX/ascorbic acid or forskolin (1 μM)/IBMX/ ascorbic acid were added to control wells. To establish conditions to assay $G_i$-coupled receptors, cells were transfected with the dopamine $D_{2L}$ plasmid DNA as described above, seeded into 96 well microtiter plates in 100 μl medium and the appropriate ligands in 100 μl medium were tested for the inhibition of forskolin-stimulated β-galactosidase activity. Each set of conditions was carried out in quadruplicate. After an eight hour exposure to ligand the cells were washed with 200 μl phosphate buffered saline and β-galactosidase activity was assayed. The plates can be stored at −20° C. for 24–72 hours before performing the β-galactosidase assay.

β-Galactosidase microassay.

β-galactosidase activity was measured with a microplate reader (Molecular Devices, Palo Alto). The assay is a modified version of the o-nitrophenyl β-D-galactoside (ONPG)-based assays of Perrin ((1963) Ann. N.Y. Acad. Sci. 81:6349–6353) and Norton and Coffin ((1985) Mol. Cell. Biol. 5:281:290). The modifications include the method of cell lysis and conditions of assay incubation as outlined below. Suppressing endogenous galactosidase activity and stabilizing the *E. coli* enzyme are critical for the success of the assay.

All the steps in the microassay were carried out at room temperature. The assay buffer is composed of 100 mM sodium phosphate, 2 mM $MgSO_4$, 0.1 mM $MnCl_2$, pH 8.0. The adherent cells were washed with PBS, the plate drained and 25 μl/well of hypotonic lysis buffer added to each well, (dilute 1 part buffer with 9 parts water). Ten minutes later 100 μl of assay buffer containing 0.5% (v/v) TritonX-100 and 40 mM β-mercaptoethanol were added. Care should be taken to avoid foaming. After an additional 10 minutes, 24 μl of ONPG (4 mg/ml in assay buffer; prepared daily) was added, and the optical density per well at 405 nm was determined with a plate reader. Readings were taken through 1.5 OD at 405 nm, within the linear portion of the color development. The initial rates, expressed as mOD/minute, are linearly related to β-galactosidase enzyme concentration over an enzyme concentration range of 0.1 to 100 mU (one unit hydrolyzes one micromole of ONPG per minute at 25 degrees, pH 7.5).

A detailed description of the screening protocol is provided in Table 1.

Example 1

Detection of β-D-galactosidase in LVIP2.OZc cells

In preliminary experiments, forskolin (5 μM) and IBMX (0.5 mM) was used to increase cyclic AMP levels. The cells were treated with the drugs for 3, 6, or 18 hours, fixed with 2% formaldehyde and 0.2% glutaraldehyde for 10 minutes at room temperature, and exposed to the chromogenic substrate, X-gal (5-bromo-4-chloro-3-indolyl-β-D-galactoside, 0.2 mg/ml) for 2 hours at 37° C. More than 90% of the cells treated with drugs for 6 to 18 hours developed a blue color. Only a few cells treated with IBMX alone turned blue. Next, the cells were transfected with human $\beta_2$-adrenergic receptor cDNA in the pcD expression vector. Seventy-two hours after the DNA was added to the cells, IBMX and ascorbic acid (100 μM) plus or minus isoproterenol (100 μM) were added to the medium. Ascorbic acid was added to prevent oxidation of isoproterenol. Six, 9 or 18 hours later, the cells were fixed and stained with 0.2 mg/ml X-gal. Unfortunately, the number of positive cells observed following treatment with isoproterenol and IBMX was much smaller than the number seen following treatment with forskolin and IBMX. It was difficult to distinguish plates of cells treated with isoproterenol and IBMX from those exposed to IBMX alone.

Therefore, a quantitative assay was developed for the cAMP-mediated increase in β-galactosidase activity. This assay was performed in 96 well plates after solubilization of the cells and incubation with the substrate ONPG. Thus, the change in optical density over a defined period of time was directly proportional to the level of β-galactosidase activity. The optical density increased linearly with time up to 1.5. The LVIP2.OZc cells were determined to contain endogenous $G_s$-coupled receptors for $PGE_2$ (prostaglandin $E_2$) and adenosine. In pilot studies, untransfected cells were treated for 8 hours with IBMX in the presence or absence of NECA [5'-(N-ETHYLCARBOXAMIDO)-ADENOSINE, adenosine $A_2$ receptor agonist], or forskolin, to increase intracellular cAMP levels (FIG. 1). NECA or forskolin-treated cells generated considerably higher levels of β-galactosidase activity than the IBMX-treated control cells. Similar results were obtained by incubations of cells with 1 or 10 μM $PGE_2$. The enzyme levels generated by 1 μM NECA, 10 μM NECA, and 0.5 μM forskolin were determined to be 8, 30, and 48-fold higher, respectively, than in the IBMX control cells. The differences were discernible by visual examination after 3 to 6 hours.

Example 2

Induction of β-galactosidase: optimizing duration of exposure to ligands and doses of ligands.

Figure 2:
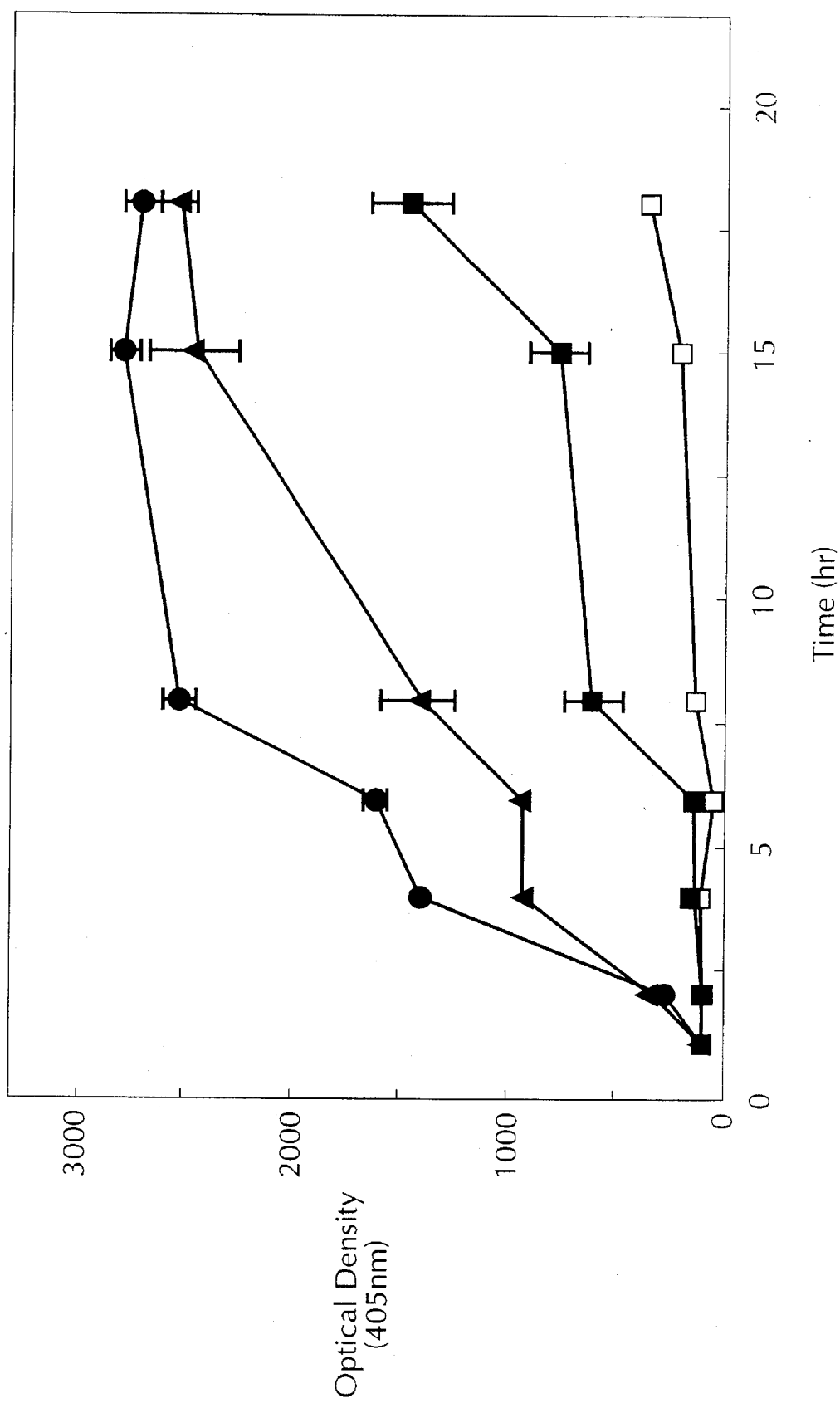
FIG. 2. Induction of β-galactosidase as a response to length of ligand exposure. LVIP2.OZc cells were incubated for 1, 2, 4, 6, 8, 12, 15 and 18 hours in control medium (containing 0.5 mM IBMX) (□), or control medium containing 0.5 μM forskolin (•), or control medium containing 1 μM NECA (■), or control medium containing 1 μM $PGE_2$ (▲). Data are mean±S.D. from one representative experiment.
Figure 3:
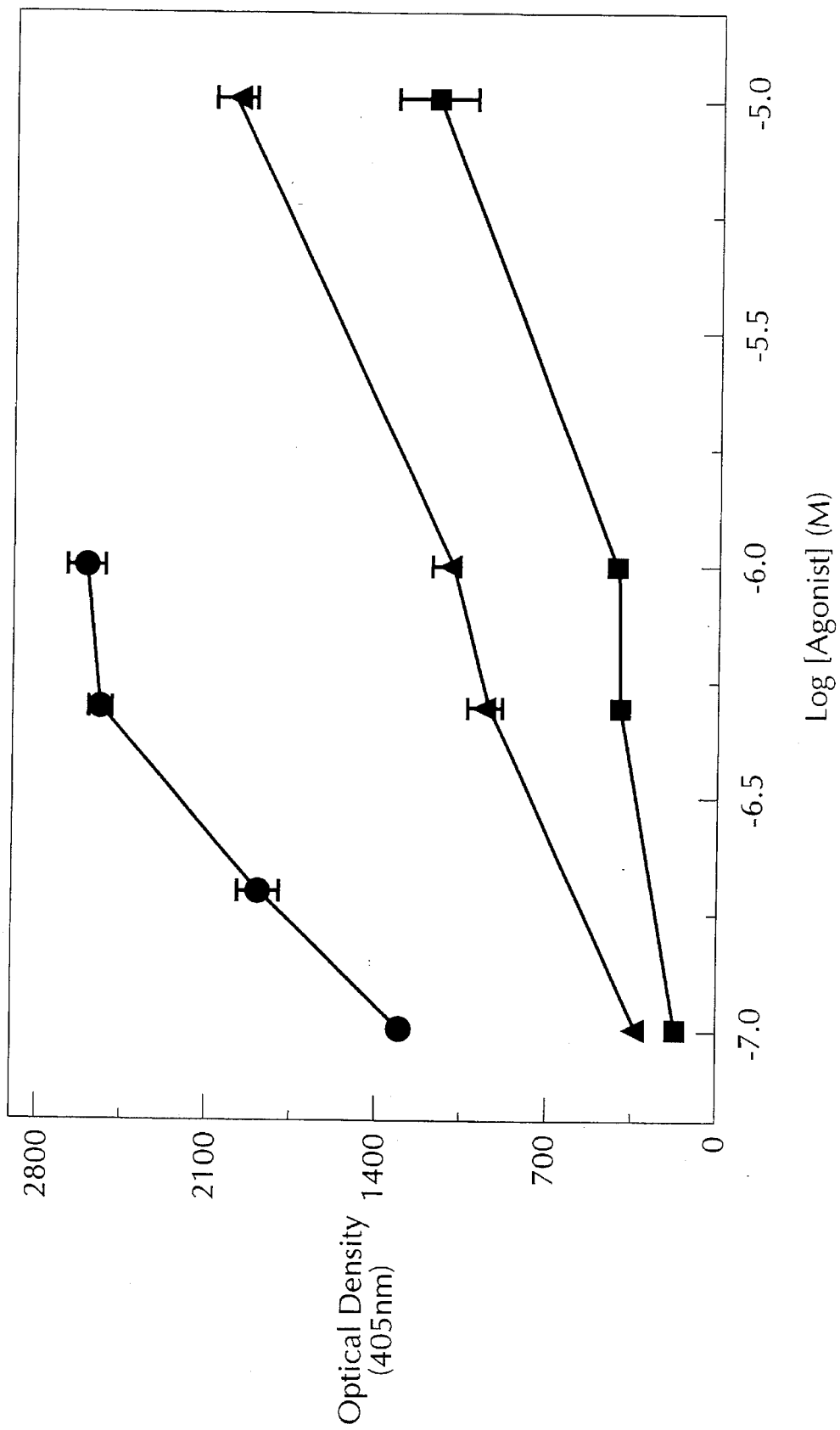
FIG. 3. Induction of β-galactosidase as a response to different doses of ligands. LVIP2.OZc cells were treated for 8 hours with control medium (containing 0.5 mM IBMX), and 0.1 or 0.2 or 0.5 or 1 μM forskolin (•), control medium and 0.1 or 0.5 or 1 or 10 μM NECA (■), control medium containing 0.1 or 0.5 or 1 or 10 μM $PGE_2$ (▲). Data are mean±S.D. from a representative experiment.

In pilot studies, cells were exposed to IBMX in the presence or absence of forskolin (0.5 μM), NECA (1 μM), or prostaglandin $E_2$ (1 μM) for 2, 4, 6, 8, 15, or 18 hours and their β-galactosidase activities measured. As shown in FIG. 2, the excellent signal to noise ratios were obtained with drug/ligand treatments of 6 to 15 hours. Dose-response data (FIG. 3) were obtained by treating cells with forskolin, NECA, or $PGE_2$ for 8 hours. Subsequent studies have shown that 6–8 hour exposures to ligand are optimal in both the $G_s$ and $G_i$ assays. Therefore, A 6–8 hour drug treatment was used; this way, the assay can be performed in one day and the signal to noise ratio is quite good. Forskolin produced its maximum effect at a 0.5 μM concentration; 10 μM prostaglandin $E_2$ and NECA were required to achieve maximum enzyme induction.

Example 3

Transfection of receptor cDNAs into LVIP2.OZc cells

The high efficiency transfection method of Chen and Okayama can be used to introduce plasmids containing receptor cDNAs into LVIP2.OZc cells. As previously shown, the amount of DNA used for transfection of cells is critically important: too little or too much DNA produces poor transient or stable expression of cDNAs. Five to 10 μg of pcD plasmid containing $β_2$-adrenergic receptor cDNA were dissolved in the calcium/BES buffered saline transfection solution and added to the 10 ml of tissue culture medium in 10 cm plates of cells. This amount of plasmid gave a punctuate precipitate which could readily be seen at 40 x magnification and which gave the best induction of β-galactosidase in response to 1 μM isoproterenol. The increase in β-galactosidase activity observed with IBMX in the presence or absence of isoproterenol was 2 to 4 times that observed with IBMX alone. The increase induced by isoproterenol was blocked by coincubation with the antagonist propranolol (1).

Example 4

Figure 4A:
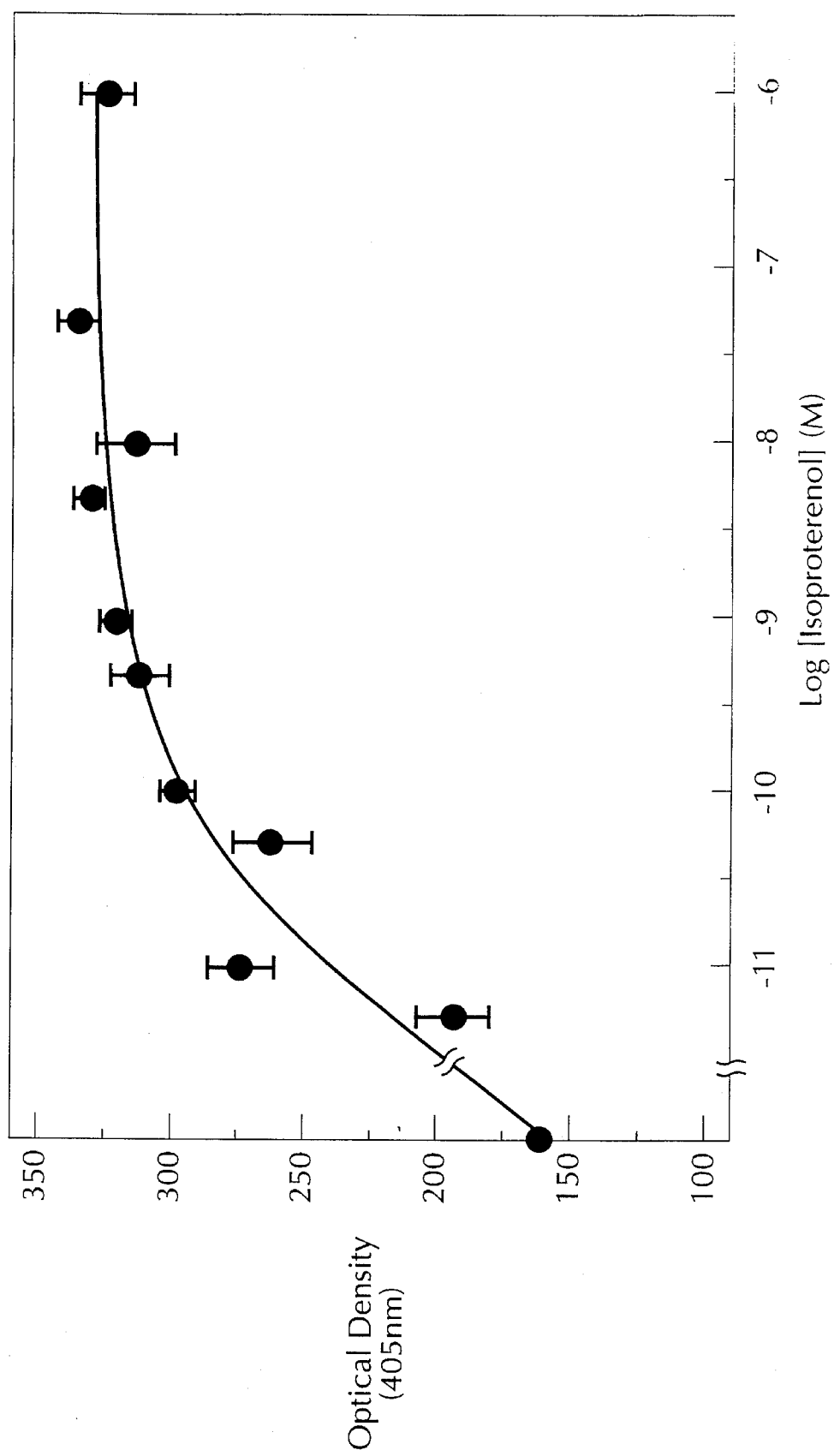
FIG. 4.A) Induction of β-galactosidase as a dose-response for $β_2$-adrenergic receptor DNA transfected LVIP2.OZc cells to isoproterenol. Cells were incubated for 8 hours with medium containing 0.5 mM IBMX, 100 μM ascorbic acid and $5 \times 10^{-12}$ to $10^{-6}$ M isoproterenol. Data are mean±S.D.
FIG. 4B) Induction of β-galactosidase as a time-response for $β_2$-adrenergic receptor DNA transfected LVIP2.OZc cells to isoproterenol. Cells were exposed for 2, 4, 6, 8, 12 and 18 hours to medium containing 0.5 mM IBMX, 100 μM ascorbic acid±1 μM isoproterenol. Data are mean±S.D. from a representative experiment.
Figure 4B:
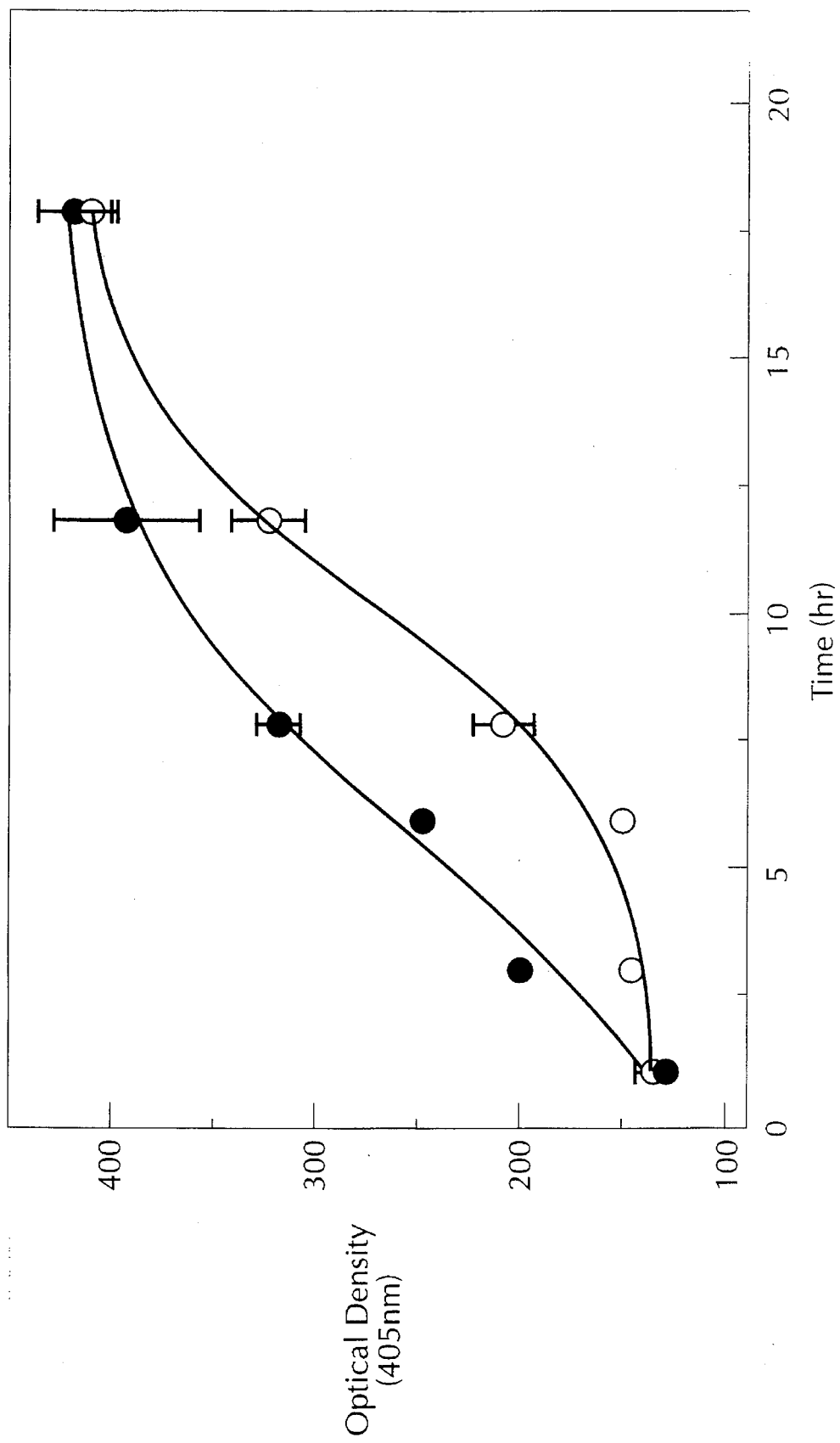

Induction of β-galactosidase in cells transfected with $β_2$-adrenergic receptor cDNA: optimizing the dose of isoproterenol and duration of exposure of cells to this compound Three days after transfection with plasmids containing the $β_2$-adrenergic receptor cDNA, LVIP2.OZc cells were seeded in 96 well plates and incubated with isoproterenol, ascorbic acid and IBMX for 8 hours. The concentration of isoproterenol was varied from $10^{-12}$ to $10^{-4}$M, a maximal effect was seen at $10^{-9}$M; no further change in optical density was obtained for concentrations between $10^{-9}$M; no further change in optical density was obtained for concentrations between $10^{-9}$ and $10^{-4}$M. The $EC_{50}$ value for isoproterenol was determined to be 10 pM (FIG. 4A). LVIP2.OZc cells were transfected as above, seeded in 96 well plates and incubated with 1 μM isoproterenol, ascorbic acid and IBMX for 2, 4, 6, 8, 12 or 18 hours. The best signal to noise ratio was found after 6–8 hours exposure to drugs (FIG. 4B).

Example 5

Inhibition of forskolin-mediated induction of β-galactosidase by aldosterone secretion inhibitory factor (ASIF)

Figure 5:
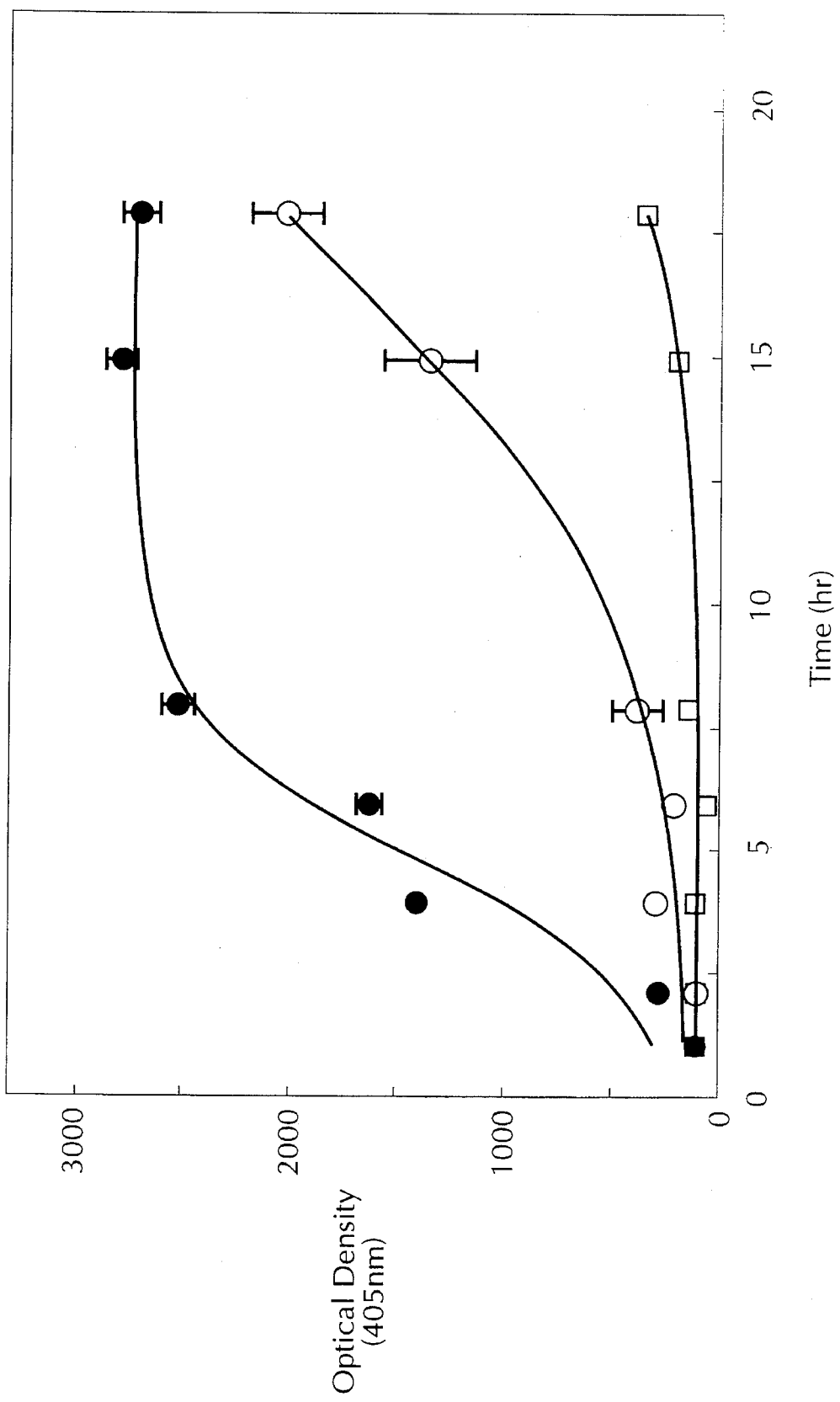
FIG. 5. Inhibition of forskolin-mediated induction of β-galactosidase by aldosterone secretion inhibitory factor during different exposure times. LVIP2.OZc cells were exposed for 1, 2, 4, 6, 8, 15, or 18 hours to control medium (containing 0.5 mM IBMX and 20 ug/ml Bacitracin) (□), or control medium containing 0.5 μM forskolin+1 μM ASIF (○), or—ASIF (•). Data are mean±S.D. from a representative experiment.

LVIP2.OZc cells were screened for endogenous receptors linked to $G_i$, which when activated would inhibit the increase in β-galactosidase activity mediated by treatment with forskolin. Among numerous agonists tested, only ASIF produced significant inhibition. ASIF was used to help optimize a screen for ligands which can interact with $G_i$-coupled receptors. Cells were treated with IBMX, IBMX and forskolin (0.5 μM), or IBMX, forskolin, and ASIF (1 μM) for 1, 2, 4, 6, 8, 15, or 18 hours. The most robust inhibition of forskolin by ASIF was observed between 6 and 8 hours (FIG. 5). Lower concentrations of forskolin (0.1 to 0.5 μM) should be used, however, to observe maximum inhibition in the assay. The highest dose of forskolin is not inhibited as well as the two lower doses, but the former may give a more reproducible level of enzyme induction.

Example 6

Figure 6A:
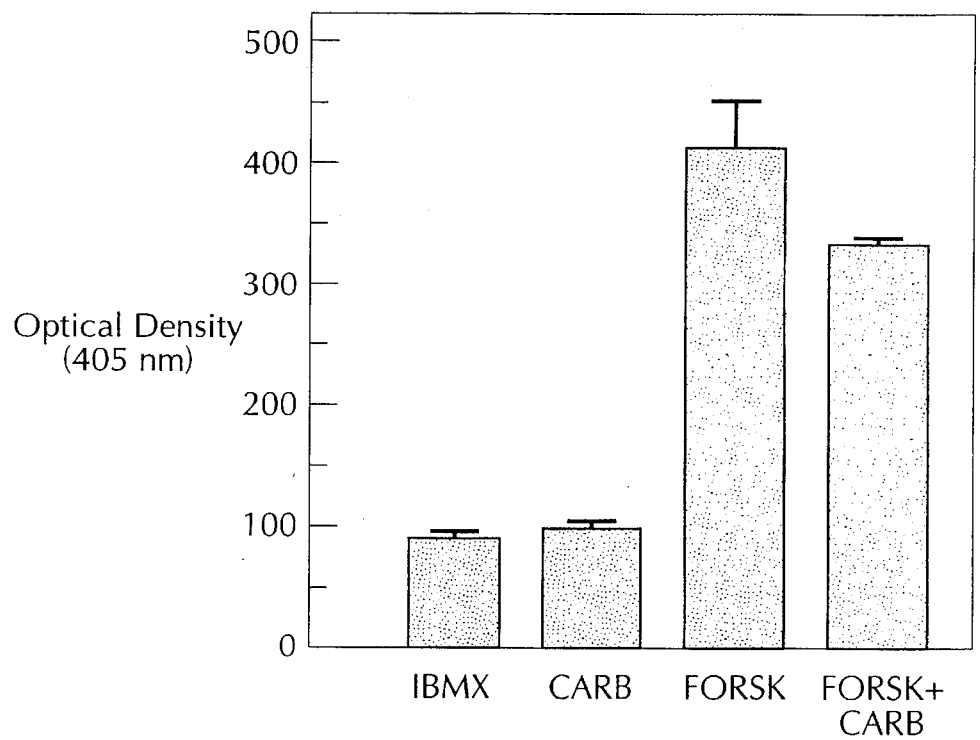
FIG. 6A) Inhibition of forskolin-mediated induction of β-galactosidase in dopamine receptor DNA transfected LVIP2.OZc cells as a dose-response to different concentrations of dopamine or quinpirole. Cells were exposed for 6 hours to medium containing 0.5 mM IBMX and 100 μM ascorbic acid and 0.5 μM forskolin±1 or 10 μM dopamine hydrochloride or 1, 10, 100 μM quinpirole hydrochloride. Data are mean±S.D. from one representative experiment.

Inhibition of forskolin-mediated induction of β-galactosidase by dopamine or quinpirole following transfection of cells with dopamine receptor cDNA Cells were transfected with 5, 10, 15, or 20 μg of $D_{2LP}$Rc/RSV, a plasmid containing the $D_{2L}$ receptor isoform. Ten μg of plasmid per 10 ml in a 10 cm dish gave the best looking precipitate, and aliquots of a suspension of cells from this dish were added to wells of a 96 well plate. Three days after the transfection, IBMX was added to all of the wells. β-galactosidase activity was elevated with forskolin (0.5 μM) alone or in combination with dopamine, or the $D_2$ selective agonist, quinpirole, to block this increase. The dopaminergic agonists were added in concentrations of 1 to 100 μM. 100 μM ascorbic acid was added to the medium to prevent oxidation of the ligands (FIG. 6A). Dopaminergic agonists alone had little or no effect on β-galactosidase levels. Significant inhibition of forskolin-stimulated increase of β-galactosidase activity was observed with either 10 μM dopamine or 10 or 100 μM quinpirole. As expected, quinpirole was more potent than dopamine.

Figure 6B:
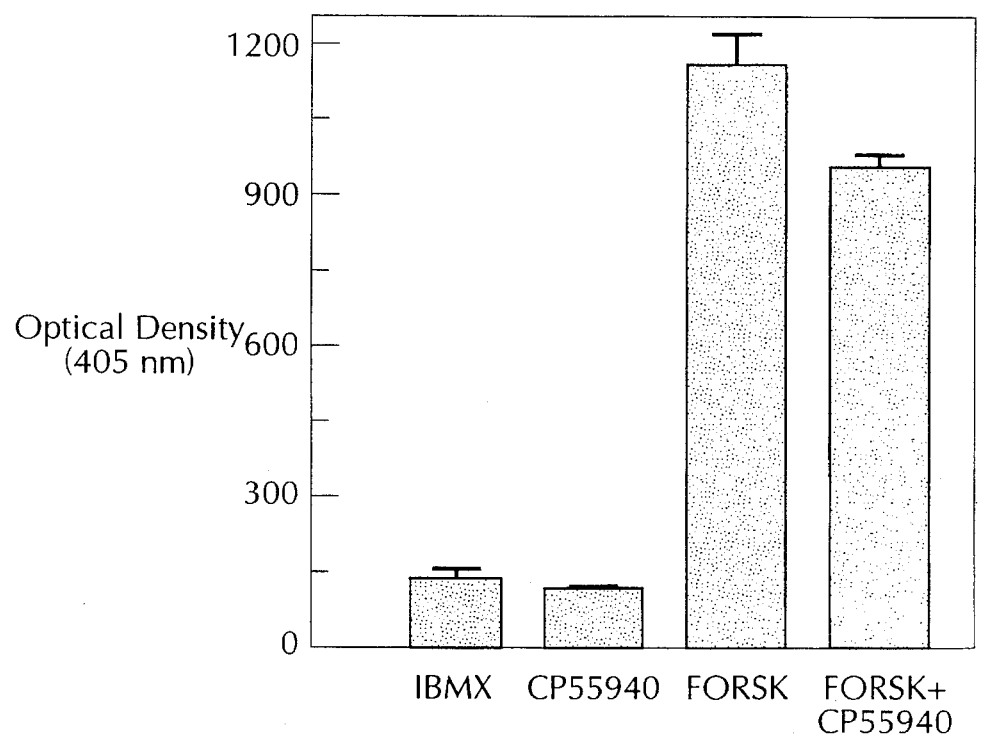
FIG. 6B) Inhibition of forskolin-mediated induction of β-galactosidase in cannabinoid receptor DNA transfected LVIP2.OZc cells by CP55940. Cells were exposed for 6 hours to medium containing 0.5 mM IBMX, 0.5 mM BSA and 0.5 μM forskolin±1 μM CP55940. Data are mean±S.D. from one representative experiment.

Transfections and assays as described above were used successfully to "diagnose" the rate cannabinoid or the human muscarinic $m_2$ receptor. Addition of 1 µM agonist CP55940 decreased forskolin stimulated activity by 15% in cells expressing the cannabinoid receptor (FIG. 6B). Similar decrease was observed after addition of 1 mM carbachol to cells expressing the muscarinic acetylcholine receptor (FIG. 6C).

TABLE 1

SCREENING PROTOCOL

| | |
|---|---|
| Day 1 | Trypzinize exponentially growing LVIP2.OZc cells, seed $5 \times 10^5$ cells/10 cm-plate, incubate overnight in 10ml growth medium. |
| Day 2 | Transfect cells with 10–20 µg plasmid DNA using $CA_3PO_4$ technique, see Materials and Methods, incubate 15 to 24 hours at 35° C. under 2–4% $CO_2$. |
| Day 3 | Wash cells 2× with growth medium, refeed, incubate 24 hours at 37° C. under 5% $CO_2$. |
| Day 4 | Trypzinize cells, pellet, seed in 96 well microtiter plates $5-10 \times 10^4$ cells/well, incubate overnight in 100 µl growth medium. |
| Day 5 | To control wells (e.g, quadruplicates) add 100 gl medium + 1 mM IBMX with (control stimulation) or without (control basal) 1 MM forskolin. To remaining wells add agonist(s) in 100 µl medium + 1 mM IBMX with ($G_i$-coupled), or without ($G_s$-coupled) 1 µM forskolin. Include antioxidants |

TABLE 1-continued

SCREENING PROTOCOL

| | |
|---|---|
| | and/or protease inhibitors as required. Incubate 6–8 hours at 37° C. under 5% $CO_2$. Wash cells with 200 µl PBS and drain. (Cells can be stored at −20° C. for 24–72 hours). |
| Day 6 | Add 25 µl diluted assay buffer/well, wait 10 minutes, then add 100 µl assay buffer, wait 10 minutes, then add 25 µl of substrate. (ONPG 4 mg/ml assay buffer). View color development visually or measure spectrophotometrically at 405 nm in a plate reader. |

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A mouse L cell line designated LVIP2.OZc having ATCC Accession No. CRL 10871.

* * * * *